United States Patent [19]

Stewart et al.

[11] Patent Number: 4,983,841
[45] Date of Patent: Jan. 8, 1991

[54] NON-INVASIVE INSPECTION

[75] Inventors: Peter A. E. Stewart; Richard T. Skelton; Martin J. Allen, all of Bristol; Joseph Douglas, Derby, all of England

[73] Assignee: Rolls-Royce plc, London, England

[21] Appl. No.: 412,337

[22] Filed: Sep. 26, 1989

[30] Foreign Application Priority Data

Oct. 4, 1988 [GB] United Kingdom ............... 8823276.4

[51] Int. Cl.$^5$ ............................................. G01T 1/169
[52] U.S. Cl. ............................... 250/358.1; 250/356.2; 250/303; 250/363.03
[58] Field of Search ................... 250/356.2, 358.1, 303, 250/363.03

[56] References Cited

U.S. PATENT DOCUMENTS

| | | | |
|---|---|---|---|
| 4,531,058 | 7/1985 | Burnham et al. | 250/363.03 |
| 4,697,079 | 9/1987 | Stewart et al. | 250/303 |
| 4,735,210 | 5/1988 | Goldenberg | 128/654 |
| 4,746,795 | 5/1988 | Stewart et al. | 250/303 |
| 4,857,736 | 8/1989 | Long | 250/358.1 |
| 4,868,392 | 9/1989 | Wong | 250/363.03 |

Primary Examiner—Constantine Hannaher
Assistant Examiner—Jacob M. Eisenberg
Attorney, Agent, or Firm—Oliff & Berridge

[57] ABSTRACT

Residual core material can be detected inside hollow cast articles using positron emission tomography. Positron radio-isotope material is inducted into any residual core material present by immersing a cast article in an aqueous solution of radio-isotope emitter, for example gallium. Absorbed gallium subsequently emits positrons which are annihilated in collisions with electrons emitting two 511 KeV gamma rays in diametrically opposite directions. The emissions are detected and tracked by a PET camera and the resulting images correlated with a sectioned image of the article as a check on the location of detected core material. Initially a low-dose-rate solution for the purpose of merely establishing the presence of core material is used but a second optional process step introduces a more active solution allowing a PET camera to collect sufficient data to image absorbed isotope.

21 Claims, 3 Drawing Sheets

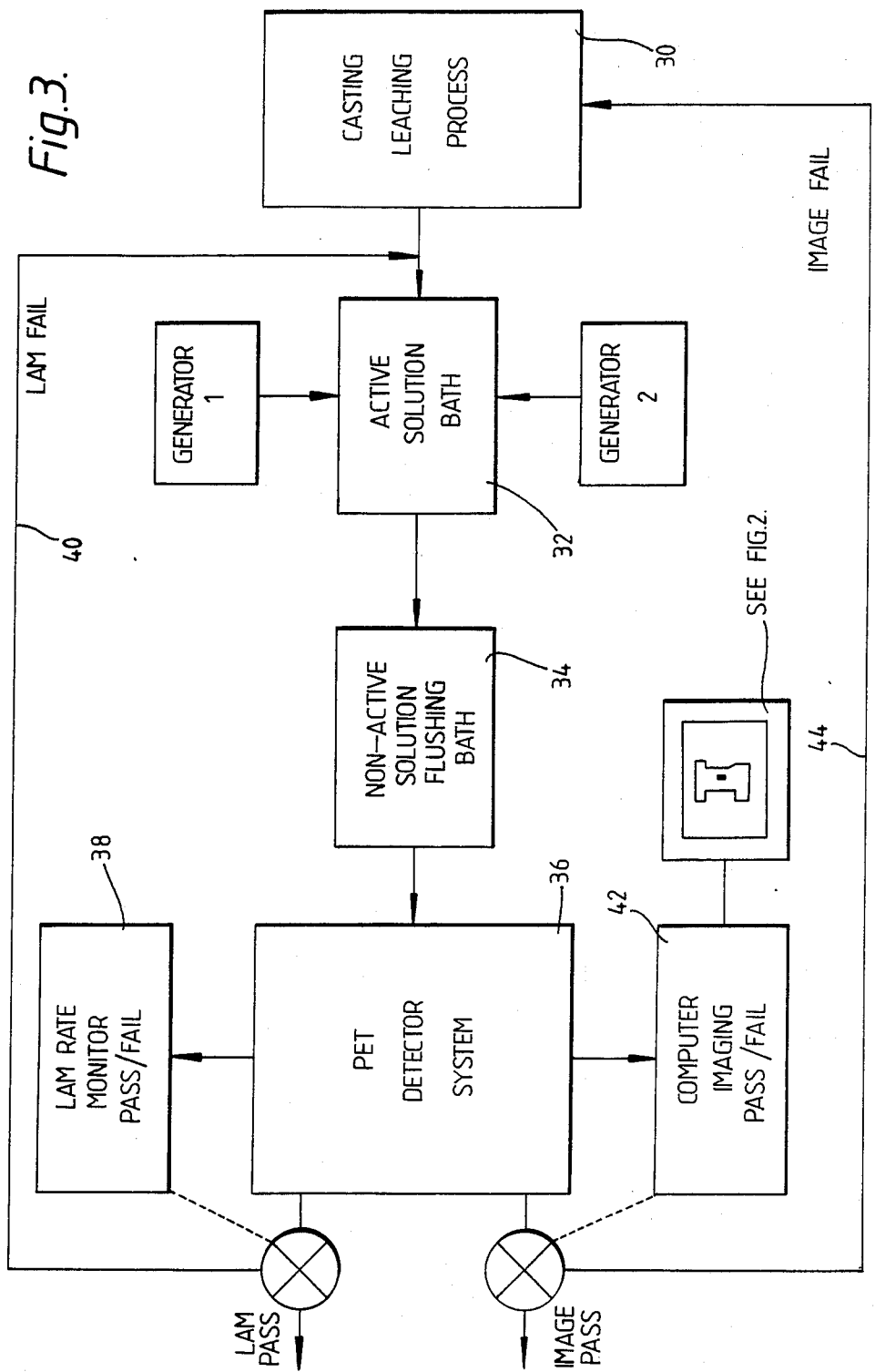

NON-INVASIVE INSPECTION

The invention relates to a method of non-invasively inspecting hollow articles, and in particular to a method of inspecting hollow cast articles to detect residual core material left behind by a preceding core removal step.

The process to be described is particularly suited to use with a lost wax process such as is used in the manufacture of air cooled turbine blades for aero engines. Currently all turbine blade castings containing intricate cooling passages are neutron radiographed in order to detect residual core material which has not been leached out correctly during the lost wax process of manufacture.

The castings are transported to neutron beam facilities where radiographs are produced. This process is expensive in neutron beam time and film costs alone, with lead times of between 2–8 weeks, and time also has to be allowed for any induced radioactivity to decay to safe levels.

It is an object of the present invention to use Positron Emission Tomography for residual core detection. This technique does not require radiograph film but uses instead computer files for image storage and can be used as an 'in-house, shop floor' process.

According to the invention there is provided a method of non-invasively inspecting a hollow article for trapped foreign matter comprising introducing into the interior of the hollow article a radio-isotope generator or emitter which is absorbed by said foreign matter, and using radiation sensitive detecting means to track emissions from substance absorbed by trapped material.

In one form of the invention a positron emission tomography (PET) technique is employed to track the source of emissions. Another form of the invention uses a single counter to monitor the emission rate from an article to determine if emitter substance has been absorbed.

Positron-emitting radioisotopes are used to label fluids which will be absorbed by the trapped material. The PET system detects a pair of 511 keV gamma rays, produced from positron-electron annihilations in absorbed fluids, which travel in diametrically opposite directions. A pair of position-sensitive detectors are placed one on either side of the object under test to detect the two annihilation gamma rays. Each of the two detectors must detect a gamma within 20 ns to be considered coincident and thus originating from a single annihilation.

The radioisotope used for this experiment is gallium 68 which has a 68 minutes half life. It is produced from a portable generator containing the germanium parent, where an elution produces a weak aqueous hydrochloric acid solution containing approximately 10 mCi of radioactivity.

The invention and how it may be carried out in practice will now be described in greater detail with reference, by way of example only, to the accompanying drawings:

FIG. 3 is a schematic of a production flow diagram utilising PET detection for residual core detection following a core leaching step.

The particular example of the invention which will be described relates to a post-casting inspection technique for air-cooled turbine blades for a jet engine. The blades which are formed with internal cooling passages are cast using the lost wax process and a ceramic core to define the internal passages. Briefly, the ceramic core is located in a female mould in the external shape of the blade and is cast in wax. An outer ceramic shell is built up by dipping the wax moulding in ceramic slurry, when this has dried the wax is melted out and leaving a ceramic shell now containing a ceramic core. This second female mould is fired and used for casting the metal blade. The outer ceramic shell can be fairly easily removed by conventional methods but the internal ceramic core has to be dissolved away using appropriate leaching solutions.

The strength and composition of these leaching solutions and the length of immersion time has been determined empirically but inevitably, not all of the ceramic core is always successfully removed in a first pass and further leaching is necessary in some cases. In order to determine which blades have to receive further treatment, neutron radiography is used to detect residual core material. Currently, castings are soaked in an aqueous solution of gadolinium nitrate which has a high neutron absorption cross-section. The residual core absorbs the solution to provide a better contrast medium for neutron radiographs.

The present proposal replaces neutron radiography by positron emission detection for locating residual core material which has been induced to take-up a positron emitter such as gallium for the purpose. On one hand the current gadolinium process could be readily adapted for the absorption of aqueous gallium. On the other hand, however, the castings can simply be immersed in an aqueous gallium solution.

Unfortunately, gallium readily bonds to metal surfaces and the relatively large surface areas of a turbine blade would attract the radioisotope and obscure the small amount of radioisotope absorbed by the core.

The amount of radioisotope absorbed by the core depends upon the specific activity of the solution, i.e. the ratio of activity (approx 10 mCi) to volume of solution. By adding gallium III, a non-active free carrier to the solution, the specific activity remains virtually unchanged. A percentage of the gallium that bonds to surfaces will now be inactive, and not contribute to image forming information.

Figure 1:
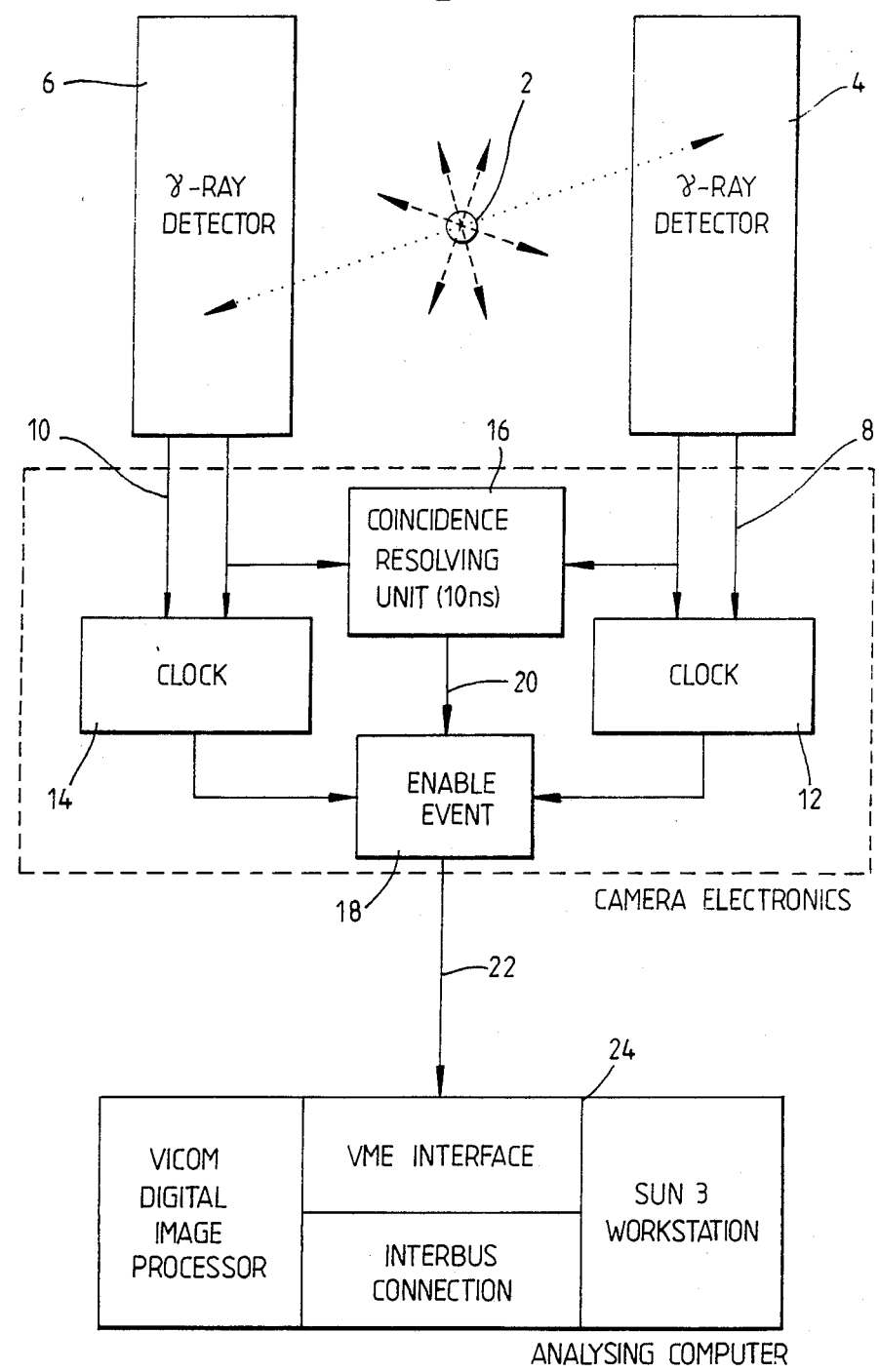
FIG. 1 is a schematic diagram of a positron emission tomography system.

The apparatus used to detect and locate positron annihilation events is shown schematically in FIG. 1 of the accompanying drawings. Apparatus of this general type is described in more detail in published British Pat. Specification No. GB 2,159,380 and in U.S. Pat. No. 4,746,795. For the purposes of the present description apparatus for use in a positron emission tomography, PET for short, system will be described in only as much detail as is necessary to gain an understanding of the present invention. A more detailed and extensive description may be had by reference to the earlier published specifications mentioned above.

Referring now to FIG. 1, an object undergoing inspection and which has been immersed in an aqueous gallium solution is located at 2 flanked on opposite sides by spatially-sensitive gamma-ray detectors 4 and 6. If the object 2 contains any material which has absorbed gallium emitter then periodically positron-electron annihilation events will occur within and in the immediate vicinity of the material giving rise to the emission of a pair of 511 keV gamma-rays in diametrically opposite directions.

The detectors 4 and 6 each comprises a two dimensional spatially sensitive array of counters. These two arrays are erected parallel with the object between them. When an annihilation occurs in the object if both gamma photons are detected simultaneously the event will be registered. By extrapolating the tracks of the two photons from the spatial locations of the activated counters within each of the arrays the intersection of these tracks with the object pin points the position of the annihilation event. Extraneous gamma photons producing single sensings in one or the other of the counter arrays are disregarded as general background noise.

The outputs 8, 10 from the detectors 4,6 respectively in FIG. 1 are connected to clock units 12, 14 and also to a coincidence resolving unit 16. The outputs essentially consist of a counter output signal tagged according to the spatial position within the array of the activated counter. The resolving unit 16 effectively applies a signal window function triggered by the first to arrive signal. This signal window is short enough to ensure effective coincidence but is long enough to accomodate delays inherent in the sensing system: typically the width of the time window is of the order of 20l nS.

The sensor signals are passed by the clock circuits 12, 14 to an event enable or gating circuit 18 which is operated on by a coincidence output 20 from the coincidence resolving circuit 16. The gated output 22 from circuit 18 comprising a pair of spatially resolved signals corresponding to a single annihilation event forms the final camera electronics output. Camera output 22 is connected to a data logging/image processing system generally indicated at 24. The data logging system registers the co-ordinates of the activated counters associated with each event. In this way, over a period of time, a data file is accumulated which can be analysed later to generate a sequence of images representing the perceived positron activity. Using a positron emission tomography technique this activity can be analysed and imaged at selected planes through the object. Image processing techniques may be employed on the images to aid analysis and interpretation. Computer software can model the three dimensional structure of the object and to superimpose on a displayed image of the object an outline or sectional drawing of the object as shown in FIG. 2.

Figure 2:
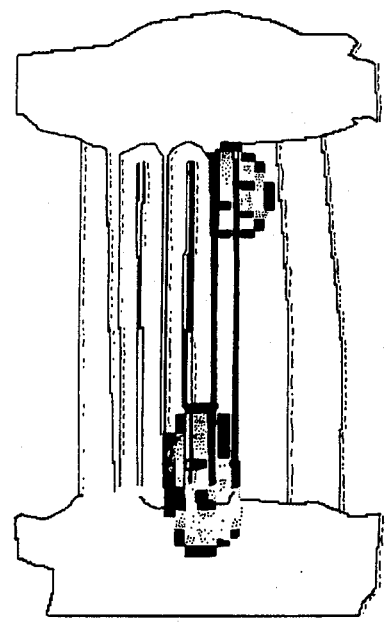
FIG. 2 shows a computer generated sectional drawing through an air cooled turbine blade superimposed on an image of the distribution of emission counts from a PET system.

FIG. 2 represents a computer generated drawing of a sectional view on a mid-plane through a turbine blade casting superimposed on a radioisotope image of the blade casting. The internal cooling passages are traced out on the computer drawing by the folded pathway running between the upper and lower platforms of the blade. The internal dividing walls separating adjacent arms of the passageway are clearly visable.

The shaded regions indicate areas which originated gamma-photon counts: the darker the shading relative to the background indicates a relatively high number of counts, and vice versa. The dark areas of shading therefore indicate an accretion of residual core material. As will be readily appreciated the particular blade sample tested has two such blockages in places where the cooling passage turns back upon itself. The blade can be returned to a leaching bath for further treatment.

FIG. 3 contains a schematic diagram of a core leaching and inspection process embodying a positron emission tomography residual core detection step. Essentially the inspection is carried out as the last stage in a casting manufacturing process. Any castings found to contain residual core material, that is which fail the PET detector test are simply sent back for releaching.

The process may be automated on a conveyer belt system. Following an initial leaching step all castings are soaked in an active solution bath comprising an aqueous hydrochloric acid solution containing radioactive gallium 68 and a small quantity of gallium III. The casting then proceeds to a non-active solution flushing bath before presentation to the PET detectors.

The PET system of FIG. 1 is based on coincident detection of gamma-rays by a pair of gas filled multiwire proportional counter detector arrays flanking the object. Each double gamma-photon detection is logged as a look-at-me (LAM) event indicating an annihilation has occurred although a certain level of background activity produces a relatively level but fairly constant count rate. Typical background activity on a laboratory trial produced about 3 LAM/s which rose to 6 LAM/s for control castings, that is castings which were clear of core material but which had been passed through the active and flushing baths. In the case of castings known to contain core material LAM rates in the range 12-30 LAM/s were recorded.

All castings emerging from the leaching process 30 follow the centre flow path in FIG. 3 passing in turn through active solution bath 32 and a clean flushing bath 34 before being presented to the PET detector system, generally indicated at 36.

On a first pass through the detector system the bath 32 contains a low dose-rate solution suitable for measuring only the LAM count rate relative to the background as indicated at 38. Those castings recording a rate in excess of a predetermined level may be returned via LAM fail path 40 to a second active solution bath similar to bath 32 for immersion in a higher dose-rate solution. Other castings deemed LAM pass move on to further production stages.

The rejected castins returned for a second immersion have their specific radioactivity increased to a level suitable for the PET imaging process. The preferred method involves returning the castings to a second bath containing a more concentrated active solution. Alternatively, the castings can be immersed in a second bath containing a different isotope generator or emitter. This second immersion will increase the signal to noise ratio of the castings enabling the PET detectors to collect sufficient data for image generation. On a second pass through the detector system 36 an image is built up along the lines of FIG. 2 using an imaging computer 42 enabling a visual inspection of the blade to be made. Those which contain residual core material are returned as indicated by return line 44 to the leaching process 30. If desired rejected castings may be returned for further leaching after the first pass by missing out the second immersion and imaging step.

In an alternative system not shown in the drawings a single gamma detector could be used to detect the 511 KeV gamma rays for the LAM rate monitor 38, see FIG. 3. However, the signal to noise ratio is low compared to that for the paired detectors used in the PET arrangment. In tests a gamma rate of 6500 counts/s due to background radiation was recorded, rising to 7500 counts/s for a clean casting, that is one which has passed through the active bath of FIG. 3 but containing no residual core material, and to 8500 counts/s for a similar casting containing residual core. This yields a signal to noise ratio of about 1.1 compared to around 5 or better for the PET system.

In yet another arrangement a scintillation detector may be used for gamma ray detection by the LAM rate monitor. A scintillator crystal about 2" diameter by 2" thick could be used for observations of typical turbine blades. The advantage of scintillator crystals is their high detection efficiency of around 40% for 511 KeV gamma rays as compared to around 10% for the multi-wire proportional counters of the PET imaging system.

We claim:

1. A method of non-invasively inspecting a hollow article for trapped foreign matter comprising:
   filling the interior of the hollow article with a mixture comprising a carrier fluid and a radioisotope capable of being absorbed by said trapped foreign matter;
   draining the mixture comprising unabsorbed radioisotope from the interior of the article; and
   using radiation sensitive detecting means to track emissions from the radioisotope absorbed by any trapped foreign matter within the hollow article.

2. A method according to claim 1, wherein the radio isotope emits positrons and the radiation sensitive detecting means is responsive to gamma-photons emitted upon annihilation of at least one of said positrons with an electron.

3. A method according to claim 2, wherein the gamma-photon emissions are tracked to source using a multi-element radiation sensitive detecting means.

4. A method according to claim 3, wherein the multi-element radiation sensitive detecting means is a positron emission tomography system.

5. A method according to claim 4, wherein the positron emission tomography system is employed to produce an image of the sources of tracked emissions.

6. A method according to claim 5, wherein an image of the hollow article undergoing inspection is superimposed on the image of emission sources.

7. A method according to claim 6, wherein said superimposed image comprises a sectional view of the hollow article.

8. A method according to claim 1, wherein the detecting means comprises a single counter for monitoring the total radiation level from the inspected hollow article.

9. A method according to claim 8, wherein the hollow article is judged to contain trapped foreign matter if a count rate of the detecting means exceeds a predetermined level.

10. A method according to claim 7, wherein an article judged to contain trapped foreign matter is recycled through said steps of:
    tracking to source the gamma-photon emissions;
    producing an image of the sources of tracked emissions; and
    superimposing an image comprising a sectional view of the object undergoing inspection on the image of emission sources, to identify the location of the trapped foreign matter.

11. A method according to claim 4, wherein the carrier fluid is an aqueous solution.

12. A method according to claim 1 further comprising a step of leaching out initial core material prior to filling the interior.

13. A method according to claim 1, wherein the step of filling the interior of the hollow article comprises immersing the hollow article in the mixture.

14. A method according to claim 1, wherein the radioisotope comprises gallium.

15. A method according to claim 14, wherein the gallium is radioactive gallium 68.

16. A method according to claim 14, wherein the mixture further comprises gallium III.

17. A method according to claim 1, wherein when the hollow article is judged to contain trapped foreign matter, the steps of filling, draining and detecting are repeated with an increased concentration of the radioisotope.

18. A method according to claim 10, wherein the radioisotope is introduced into the hollow article in the mixture comprising an aqueous solution, gallium and gallium III.

19. A method according to claim 18 further comprising a first step of leaching out initial core material.

20. A method according to claim 18, wherein the step of filling the interior of the hollow article comprises immersing the hollow article in the mixture.

21. A method according to claim 1, wherein when the hollow article is judged to contain trapped foreign matter, the steps of filling, draining and detecting are repeated with a second radioactive isotope different from said radioisotope.

* * * * *